United States Patent [19]

Sharma et al.

[11] Patent Number: 5,739,342
[45] Date of Patent: Apr. 14, 1998

[54] PROCESS FOR THE PREPARATION OF NICOTINIC ACIDS

[75] Inventors: Padam N. Sharma, Gurnee; Marazban H. Vandrevala, Libertyville, both of Ill.

[73] Assignee: Abbott Laboratories, Abbott Park, Ill.

[21] Appl. No.: 811,087

[22] Filed: Mar. 3, 1997

[51] Int. Cl.$^6$ .................................................. C07D 213/55
[52] U.S. Cl. ............................................ 546/318; 546/315
[58] Field of Search ..................................... 546/318, 315

[56] References Cited

U.S. PATENT DOCUMENTS

| | | | |
|---|---|---|---|
| 4,616,019 | 10/1986 | Chu | 514/254 |
| 4,649,144 | 3/1987 | Matsumoto et al. | 514/300 |
| 4,840,954 | 6/1989 | Petersen et al. | 514/254 |
| 5,204,478 | 4/1993 | Jennings et al. | 546/315 |

FOREIGN PATENT DOCUMENTS

| | | |
|---|---|---|
| 0153580 | 9/1985 | European Pat. Off. |
| 0160578 | 11/1985 | European Pat. Off. |
| 0302372 | 2/1989 | European Pat. Off. |
| 0333020 | 9/1989 | European Pat. Off. |

OTHER PUBLICATIONS

Chu, D., et al., "Synthesis and Structure-Activity Relationships of New Arylfluoronaphthyridine Antibacterial Agents", *J. Med. Chem.*, vol. 29, No. 11, pp. 2363-2369, 1986.

Mann, F., et al., "The Synthesis and Properties of 1:7-Dialkyl Xanthines", University Chemical Laboratory, Cambridge, pp. 751-760, 1945.

White, E., "The Chemistry of the N-Alkyl-N-nitrosoamides. I. Methods of Preparation", Contribution No. 1262 From the Sterling Chemistry Laboratory, Yale University, vol. 77, pp. 6008-6010, Nov. 20, 1955.

White, E., "The Chemistry of the N-Alkyl-N-nitrosoamides. II. A New Method For The Deamination of Aliphatic Amines", Contribution No. 1263 From the Sterling Chemistry Laboratory, Yale University, vol. 77, pp. 6011-6014, Nov. 20, 1955.

*Primary Examiner*—C. Warren Ivy
*Assistant Examiner*—Charanjit S. Aulakh
*Attorney, Agent, or Firm*—Mona Anand

[57] ABSTRACT

The present invention relates to an improved process for the preparation of nicotinic acids represented by the following structural formula (I):

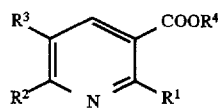

which are prepared by reacting a nicotinic amide compound having the formula:

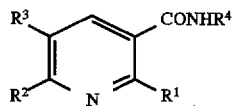

under acidic conditions with a nitrite salt. In the process of the invention have the groups $R^1$, $R^2$, and $R^3$, in the compounds are independently selected from the group consisting of hydrogen, and halogen atoms and $R^4$ is selected from the group consisting of hydrogen, lower alkyl and aryl. The process provides the nicotinic acid compounds in improved yields.

10 Claims, No Drawings

PROCESS FOR THE PREPARATION OF NICOTINIC ACIDS

TECHNICAL FIELD

The present invention relates to an improved process for the preparation of nicotinic acids and derivatives of nicotinic acid. The process uses nitrite salts to convert nicotinic amides to acids or esters.

BACKGROUND OF THE INVENTION

Substituted pyridines are useful as intermediates for the synthesis of naphthyridine antibacterial agents. 2,6-Dichloro-5-fluoronicotinic acid is of particular interest because it is a key intermediate in the synthesis of naphthyridine antibacterial agents. (See for example, European Published Patent Applications 132,845, 160,578, 153,580 and U.S. Pat. Nos. 4,840,954, 4,649,144, 4,616,019, and Chu, D. T. W., et al., *J. Med. Chem.*, 29, 2363–2369 (1986)). Several of these references disclose a process for preparing nicotinic acid. However, many of the processes provide the product in low overall yield, about 50–60%.

European Patent Application 333 020 discloses a process for preparing 2,6- dichloro-5-fluoronicotinic acid starting from inexpensive starting materials, ethyl formate, ethyl fluoro acetate, and cyanoacetamide. However, in this process purification procedures are required to remove byproducts. Another drawback is the low overall yield (40%–45%) in converting 2,6-dihydroxy-3-cyano-5-fluoropyridine to 2,6-dichloro-5-fluoronicotinic acid.

U.S. Pat. No. 5,204,478 discloses the preparation of 2,6-dichloro-5-fluoronicotinic acid and 2,6-dichloro-5-fluoronicotinoyl chloride. The process described converts a 2,6-dihydroxy-5-fluoronicotinic acid ester into 2,6-dichloro-5-fluoronicotinoyl chloride. The ester is converted using phosphorus oxychloride and a lithium reagent to 2,6-dichloro-5-fluoronicotinoyl chloride in one step. This is followed by conversion, by basic hydrolysis, to afford 2,6-dichloro-5-fluoronicotinic acid.

It would be advantageous to have a method for the preparation of nicotinic acid derivatives which provides nicotinic acid derivatives in high yields and high purity.

It would be advantageous to have a method for the preparation of nicotinic acid derivatives which eliminated the need for purification of intermediate compounds.

SUMMARY OF THE INVENTION

The present invention relates to a process for preparing compounds represented by the following structural formula (I):

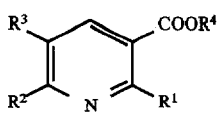
I which are prepared by reacting a compound having the formula:

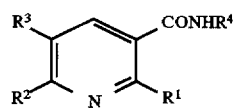

under acidic conditions with a nitrite salt. The $R^1$, $R^2$, and $R^3$, groups are independently selected from the group consisting of hydrogen, and halogen atoms and the $R^4$, is selected from the group consisting of hydrogen, lower alkyl and aryl.

DETAILED DESCRIPTION OF THE INVENTION

It has surprisingly been found that nicotinamides can be converted, in high yield and purity, to nicotinic acids with nitrite salts in the presence of an acid. The process described provides an efficient method for the preparation of nicotinic acids which eliminates the need for additional purification of the intermediate or final products. This process utilizes a new method for the preparation, inexpensive starting materials, and a more efficient solvent for extraction of the product, without the need for methylene chloride solvent. This method affords higher yields than the previous methods.

The process for preparing compounds represented by formula (I):

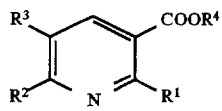
I comprises the step of reacting a compound having the formula:

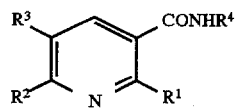

with a nitrite salt, under acidic conditions. The groups, $R^1$, $R^2$, and $R^3$, are independently selected from the group consisting of hydrogen, and halogen atoms and the $R^4$ group is selected from the group consisting of hydrogen, lower alkyl and aryl.

The nitrite salts which are useful in practicing the present invention are alkali metal salts having the formula $MNO_2$ where M is an alkali metal. Non-limiting examples of alkali metal salts useful in the present invention include salts such as, sodium nitrite, lithium nitrite, potassium nitrite and the like. As used herein, the term "alkyl" means a straight or branched hydrocarbon radical having from one to six carbon atoms and includes, for example, methyl, ethyl, n-propyl, isopropyl, n-butyl, secondary butyl, isobutyl, tertiary butyl, n-pentyl, n-hexyl, and the like. Preferably the $R^4$, groups are hydrogen, methyl, or ethyl.

As used herein, the term "aryl", refers to carbocyclic aromatic radicals, such as, phenyl, benzyl, naphthyl, and the like.

As used herein the term "alkali metal" is a metal in Group IA of the periodic table and includes metals such as, lithium, sodium, potassium, and the like.

Abbreviations

Abbreviations which have been used in the descriptions of the scheme and the examples that follow are, DMSO for dimethyl sulfoxide, DCE for 1,2-dichloroethane; HPLC for high performance liquid chromatography, MeOH for methanol, MTBE for Methyl tert-butyl ether; $PCl_5$ for phosphorus pentachloride; and $POCl_3$ for phosphorus oxychloride.

Synthetic Methods

The compounds and processes of the present invention will be better understood in connection with the following synthetic schemes which illustrate the methods by which the compounds of the invention may be prepared. The groups $R^1$, $R^2$, $R^3$, and $R^4$, are as defined above unless otherwise noted below.

The nicotinic acids, I are prepared starting from a nitrile having formula II and hydrolyzing it to an amide, formula III. The amide is reacted with a nitrite salt under acidic conditions to provide the nicotinic acid, I. The use of nitrite salts allows the reaction to be performed without the need for purification of the nicotinamide, III or the product acid, I saving time and improving the yield. This is illustrated in Scheme I, below.

SCHEME I

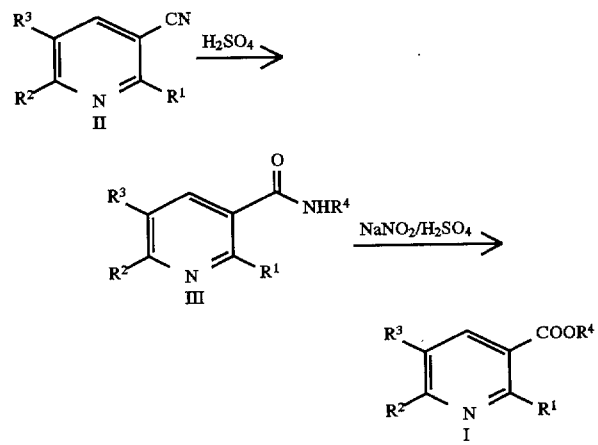

A preferred embodiment for preparing the nicotinic acids is illustrated in Scheme II. The 2,6-dihydroxy-3-cyano-5-fluoropyridine (1) is prepared according to the method described in European Patent Application 333 020 (EP 020), incorporated herein by reference. This document describes the preparation of 2,6-dihydroxy-3-cyano-5-fluoropyridine starting with ethyl formate, ethyl fluoro acetate, and cyanoacetamide. The ethyl formate and ethyl fluoro acetate, are initially reacted in the presence of sodium methoxide, followed by addition of cyanoacetamide to provide the dihydroxy cyanopyridine (1). The 2,6-dihydroxy-3-cyano-5-fluoropyridine is converted to 2,6-dichloro-3-cyano-5-fluoropyridine (2) with phosphorus oxychloride ($POCl_3$) and phosphorus pentachloride ($PCl_5$). The 2,6-dichloro-5-fluoro-3-cyanopyridine is hydrolyzed to 2,6-dichloro-5-fluoronicotinamide (3) by heating the cyano compound in the presence of concentrated sulfuric acid. The 2,6-dichloro-5-fluoronicotinic acid (4) was prepared by reaction of the amide (3) with sodium nitrite under aqueous acidic conditions.

SCHEME II

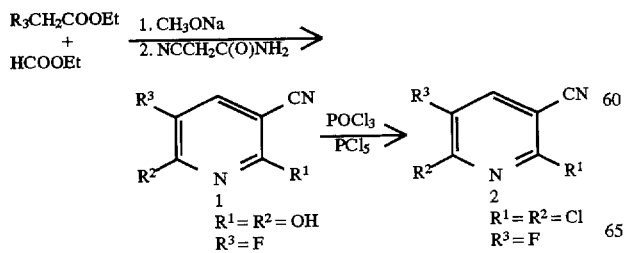

-continued
SCHEME II

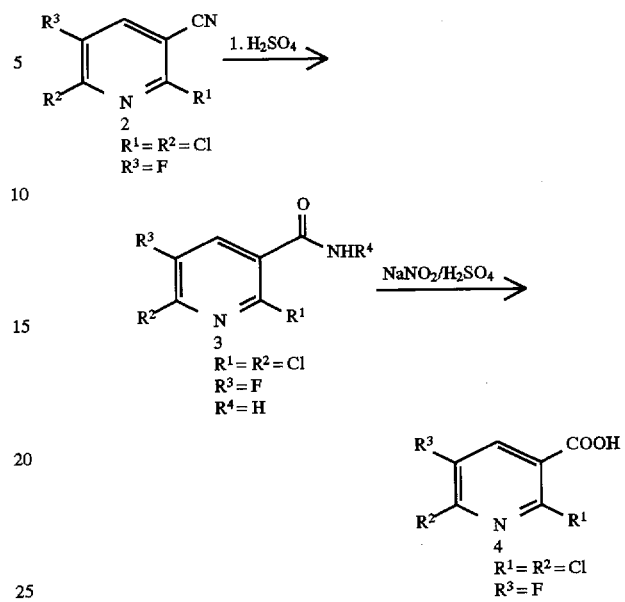

DESCRIPTION OF THE PREFERRED EMBODIMENTS

The compounds and processes of the present invention will be better understood in connection with the following examples, which are intended as an illustration of and not a limitation upon the scope of the invention.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The compounds prepared in Examples 1b and 1c were analyzed by HPLC. The analyses were performed on a Shimadzu HPLC instrument, using a variable wavelength UV detector at 284 nm and a 30 cm×3.9 mm Waters μ-Bondpack C-18 column. The mobile phase was 64% by volume 0.5M citric acid solution (9.6 g/L, HPLC grade water) and 36% by volume acetonitrile (HPLC grade). The flow rate was 2 mL/minute and the injection volumes were about 10–20 μL.

EXAMPLE 1

Preparation of 2,6-Dichloro-5-fluoronicotinamide (3)

1a. Preparation of 2,6-Dihydroxy -5-fluoro-3-cyanopyridine (1)

A 300 gallon reaction vessel was charged with 300 L of toluene, blanketed with nitrogen and 30.6 kg of sodium methoxide was added. This was followed by 62.6 kg of ethyl formate. The temperature was maintained below 30° C.

Ethyl fluoroacetate, 30 kg, was added to the mixture. (Extreme caution must be used when working with ethyl fluoroacetate. Ethyl fluoroacetate is highly toxic). The ethyl formate and ethyl fluoroacetate were metered to maintain the temperature at about 30° C. The reaction mixture was allowed to stir for 3 to 5 hours and formed a suspension. The suspension was allowed to cool to 5°–10° C. and cyanoacetamide, 71.4 kg, was added. This formed a thick suspension which was diluted with about 300 L of methanol, allowed to warm to room temperature (about 20° C.) and stirred for an additional 12–16 hours. Glacial acetic acid, 35.6 L, and water, 200 L, were added to the suspension. The suspension was centrifuged to separate the product. The product was collected and dried. The title compound, M. W. 154.10, had a purity of 95%, by HPLC, and m.p. 135°–140° C.

1b. Preparation of 2,6-Dichloro-5-fluoro-3-cyanopyridine (2)

A 12 liter (L) reaction vessel equipped with a mechanical stirrer, thermometer, condenser and nitrogen inlet was added 2000 mL of phosphorus oxychloride ($POCl_3$). The vessel was cooled to 5°–10° C., and 500 g of dry 2,6-Dihydroxy-5-fluoro-3-cyanopyridine (2. 1% moisture: dried at 115° C. under vacuum overnight) was added in portions, keeping temperature below 30° C. The mixture was heated at 80°–85° C. for 60 minutes and allowed to cool to room temperature. Phosphorus pentachloride ($PCl_5$), 2200 g, was added, in portions, to the mixture. After the addition was complete the mixture was heated to 100°–104° C. and monitored by HPLC, at 24 hours, 93% product and 30 hours, 95% product. The reaction was stopped after about 30 hours. The mixture was cooled down to room temperature and $POCl_3$ was removed under reduced pressure (temperature 30°–60° C.). 1,2-Dichloroethane (DCE), 2.0 L, was added to the residue and the mixture was cooled to 5°–10° C. in an ice bath. Distilled water, 5000 mL, was added slowly to the mixture, maintaining the temperature below 40° C. After the water addition the mixture was stirred at room temperature for an hour. The 1,2-dichloroethane (DCE) layer was separated and the aqueous layer was extracted with DCE (2×1000 ml). The DCE extracts were combined. The DCE was removed by vacuum distillation. The residual 2,6-dichloro-5-fluoro-3-cyanopyridine product is used in situ for next step.

1c. Preparation of 2,6-Dichloro-5-fluoronicotinamide (3)

The amide was prepared from the 2,6-dichloro-5-fluoro-3-cyanopyridine described in Example 1b. The cyanopyridine was placed in 12 L flask, cooled to 5°–10° C. in an ice bath, and 2300 mL of concentrated sulfuric acid was added. The residual DCE was then removed under vacuum at room temperature. After removal of the DCE the mixture was heated at 65°–70° C. for 1–2 hours and monitored by HPLC. After about 2 hours the mixture was cooled to about 10° C. in an ice bath. The amide product (3) formed was used directly for the next step without isolation or purification.

EXAMPLE 2

Preparation of 2,6-Dichloro-5-fluoronicotinic acid (4)

An aqueous sodium nitrite ($NaNO_2$) solution, prepared from 400 g of sodium nitrite in 500 m/of distilled water, was added dropwise, under the surface of the acidic amide reaction mixture from Example 1c, maintaining temperature between 35°–40° C. An exotherm up to 50° C. was observed towards the end of addition of sodium nitrite solution. (The exotherm may be avoided by increasing the amount of sulfuric acid). The reaction mixture became thick and required thorough mixing. After the addition of the sodium nitrite solution, the reaction mixture was stirred for about 15 minutes, warmed to 45°–50° C., and monitored by HPLC. After about 3 hours the reaction mixture was cooled to 0°–5° C., and 5000 mL of distilled water was added slowly, maintaining the temperature below about 30° C. The mixture was stirred at room temperature for 60 minutes. Methyl tert-butyl ether (MTBE), 2000 mL, was added and the mixture was stirred at room temperature for an additional 30 minutes. The MTBE layer was separated and the aqueous layer was extracted with MTBE (2×1000 mL). The combined MTBE layers were washed with distilled water (1×500 ml). The combined MTBE layer was mixed with 10% aqueous sodium carbonate solution (2 L). The mixture was stirred at room temperature for about 30 minutes to extract the acid product into the aqueous layer. The aqueous layer was separated, and the MTBE layer was discarded. The aqueous layer was cooled to 10°–15° C. and acidified to pH<2 with concentrated HCl, about 310 mL, to precipitate the solid product. The product was filtered and washed with water (2×500 mL). This solid was dried at 65° C. under vacuum and nitrogen bleeding for 20 hours. The dry weight was 518.3 g and was 99.9% pure by HPLC, w/w. The overall yield of 2,6-dichloro-5-fluoronicotinic acid (4) was 76%, based on 2,6-dihydroxy-5-fluoro-3-cyanopyridine.

The 2,6-dichloro-5-fluoronicotinic acid product (4) was analyzed by HPLC, and compared to an authentic sample using an Alltech Hypersil BDS C-18, 150×4.6 mm column. The mobile phase was 25% by volume Methanol (HPLC grade) and 75% by volume 0.05M $KH_2PO_4$ buffer. (The buffer was prepared from 6.8 g of $KH_2PO_4$ in 1 L of D.I. water and 5.0 mL of triethylamine. The buffer was acidified to pH 2.5 with phosphoric acid.) The flow rate was 1.0 ml/minute and the detector wavelength was 284 nm.

COMPARATIVE EXAMPLE 2

Preparation of 2,6-Dichloro-5-fluoronicotinic acid (4)

2b. Preparation of 2,6-Dichloro-5-fluoro-3-cyanopyridine (2)

A 300 gallon reaction vessel was charged with 300 kg of phosphorous oxychloride ($POCl_3$), cooled and blanketed with nitrogen. To the cooled $POCl_3$ was added phosphorus pentachloride ($PCl_5$), 182 kg, and 30 kg of the dried 2,6-Dihydroxy-5-fluoro-3-cyanopyridine (prepared in Example 1a). The mixture was heated at reflux for 20–24 hours and allowed to cool to room temperature. The $POCl_3$ was removed under reduced pressure. Methylene chloride, about 473 L, was added and the mixture was cooled to 5°–10° C. in an ice bath. The methylene chloride/reaction mixture was slowly added to ice water, about 360 kg, maintaining the temperature at 0° C. with external cooling. After addition to the water the mixture was stirred to decompose the $PCl_5$. The methylene chloride layer was separated, dried and filtered. The methylene chloride was removed by distillation. The residual 2,6-dichloro-5-fluoro-3-cyanopyridine product is used in situ for next step.

2c. 2,6-Dichloro-5-fluoronicotinamide (3)

The amide was prepared by addition of concentrated sulfuric acid, 185 kg, to the 2,6-dichloro-3-cyano-5- fluoropyridine (2) residue prepared in Example 2b. The mixture was heated at about 75° C. for 1 hour. The solution was cooled and added to 360 kg of ice water. The suspension formed was extracted with isopropyl alcohol/chloroform (30:70). The organic layer was removed and dried. The solvent was evaporated to provide the title compound.

2d. Preparation of 2,6-Dichloro-5-fluoronicotinic acid (4)

The acid was prepared directly from the 2,6-dichloro-5-fluoronicotinamide (3), described in Example 2c, without purification. The nicotinamide (3), was placed in a flask, and concentrated hydrochloric acid, 327 kg, was added. The mixture was heated at reflux for about 2 hours. The reaction mixture was cooled in an ice bath to provide a solid product. The overall yield of 2,6-dichloro-5-fluoronicotinic acid (4) was 55%, based on 2,6-dihydroxy-5-fluoro-3-cyanopyridine.

2e. Alternative Preparation of 2,6-Dichloro-5-fluoronicotinic acid (4)

Alternatively, a one step hydrolysis of 2,6-dichloro-5-fluoro-3-cyanopyridine (2) can be accomplished as follows: The cyanopyridine (2), 28 g, was added to a flask containing concentrated sulfuric acid, 26 mL. The mixture was heated at about 75° C. for about 45 minutes. The solution was cooled in an ice bath and concentrated hydrochloric acid, 130 mL was added dropwise. The mixture was heated at reflux for about 1 hour. The mixture was allowed to cool to room temperature and then cooled in an ice bath. The precipitate was filtered to provide 6 g of 2,6-dichloro-5-fluoronicotinic acid.

It will be understood that the specification and the examples are illustrative and not limitative of the present invention and that other embodiments within the spirit and scope of the invention will suggest themselves to those skilled in the art.

What is claimed is:

1. An improved process for the preparation of compounds having the formula:

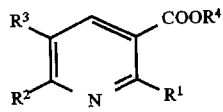

said process comprising reacting a compound having the formula:

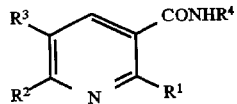

under acidic conditions with a nitrite salt;

wherein $R^1$, $R^2$, and $R^3$, are independently selected from the group consisting of hydrogen, and halogen atoms and $R^4$ is selected from the group consisting of hydrogen, lower alkyl, and aryl.

2. The process according to claim 1, wherein $R^4$ is hydrogen or lower alkyl.

3. The process according to claim 2, wherein $R^4$ is hydrogen.

4. The process according to claim 2, wherein $R^4$ is lower alkyl selected from the group consisting of methyl, ethyl and propyl.

5. The process according to claim 1, wherein $R^1$, $R^2$, and $R^3$ are halogen atoms.

6. The process according to claim 5, wherein the halogen atoms are selected from the group consisting of chlorine, bromine and fluorine.

7. The process according to claim 1, wherein $R^1$, and $R^2$, are chlorine, $R^3$ is fluorine and $R^4$ is hydrogen.

8. The process according to claim 1 wherein the nitrite salt is a salt of a Group IA metal.

9. The process according to claim 1 wherein the Group IA metal is selected from the group consisting of sodium, potassium, and lithium.

10. The process according to claim 1 wherein the Group IA metal is sodium.

* * * * *